United States Patent [19]
Soika et al.

[11] Patent Number: 5,284,481
[45] Date of Patent: Feb. 8, 1994

[54] COMPACT COLLAPSIBLE INFUSION APPARATUS

[75] Inventors: Emil H. Soika, Poway; Steven R. Payne, San Diego, both of Calif.

[73] Assignee: Block Medical, Inc., Carlsbad, Calif.

[21] Appl. No.: 984,899

[22] Filed: Dec. 2, 1992

[51] Int. Cl.⁵ .................................. A61M 37/00
[52] U.S. Cl. ............................. 604/132; 206/438; 206/370; 222/105
[58] Field of Search ............... 604/132, 133, 140, 142, 604/153; 222/105, 106, 107, 103, 95; 206/438, 363, 370, 820, 461, 462, 571; 128/DIG. 12

[56] References Cited

U.S. PATENT DOCUMENTS

| | | | |
|---|---|---|---|
| 2,660,339 | 11/1953 | Koob | 222/105 |
| 3,412,906 | 11/1968 | Dinger | 128/DIG. 12 |
| 3,759,375 | 9/1973 | Nappi | 206/370 |
| 4,386,929 | 6/1983 | Peery et al. | 604/132 |
| 4,507,116 | 3/1985 | Leibinsohn | 128/DIG. 12 |
| 4,522,302 | 6/1985 | Paikoff | 206/571 |
| 4,645,079 | 2/1987 | Hill | 206/370 |
| 4,915,693 | 4/1990 | Hessel | 604/132 |
| 4,953,753 | 9/1990 | Gortz | 222/105 |
| 5,080,652 | 1/1992 | Sancoff et al. | 604/132 |
| 5,105,983 | 4/1992 | Sancoff et al. | 222/103 |
| 5,137,175 | 8/1992 | Kowalski et al. | 222/105 |
| 5,178,610 | 1/1993 | Tsujikawa et al. | 128/DIG. 12 |

Primary Examiner—John G. Weiss
Attorney, Agent, or Firm—Baker, Maxham, Jester & Meador

[57] ABSTRACT

A liquid infuser apparatus includes an elastic sleeve mounted on an elongated member and within a collapsible spherical housing to enable it to expand naturally to maintain a constant pressure over the infusion period. A rigid open ended housing into which an infuser may be removeably placed provides a reusable protective housing. Multiple infusers are packaged with a rigid housing in a kit.

28 Claims, 5 Drawing Sheets

COMPACT COLLAPSIBLE INFUSION APPARATUS

BACKGROUND OF THE INVENTION

The present invention relates to liquid dispensing apparatus and pertains particularly to an improved infusion apparatus for delivering intravenous drugs at a controlled rate to a patient.

It is often necessary to intravenously supply patients with pharmaceutically active liquids at a controlled rate over a long period of time. It is desirable that this be accomplished while the patient is in an ambulatory state. A few devices have been developed in the past for accomplishing this purpose.

The prior art devices typically comprise an elastic bladder forming a liquid container mounted in an elongated cylindrical housing, and having a flow control valve or device and tubing for supply of the liquid to the patient. These devices are constructed with the cylindrical form in order to provide a compact arrangement. The elastic walls of the bladder are forced to expand along the walls of the cylindrical housing when filled with the liquid, and provide the pressure for expelling the liquid. These prior art devices are typically filled by hand by means of a syringe which often require an inordinate amount of force.

Another drawback to the prior art devices is that the bladder is forced to expand into an unnatural elongated configuration along the housing walls as the container is filled. As a result of this unnatural configuration, the pressure of the bladder and the flow rate of the unit varies widely with the volume of liquid therein. Therefore, they do not have a reasonably stable pressure and flow rate over the infusion period.

Prior U.S. Pat. Nos. 5,080,652, dated Jan. 14, 1992 and 5,105,983, dated Apr. 21, 1992 of common assignment herewith disclose recently developed improved infusion devices. These devices have an inflatable elastic bladder that is allowed or inflate naturally at a substantially uniform pressure. A hard protective housing accommodates natural spherical inflation of the bladder to its rated capacity or volume.

While these improved devices are portable and convenient to use, one objection is that the housing is rigid and space consuming. This increases the cost of packaging, storage and shipment. It also increases the cost of manufacture because the housing must also be sterilized. Therefore, it would be desirable to have a housing that is collapsible and/or reusable.

It is desirable that the housing of an inflatable bladder infuser be compact and inexpensive to manufacture and ship.

Accordingly, it is desirable that an improved infuser apparatus be available.

SUMMARY AND OBJECTS OF THE INVENTION

It is the primary object of the present invention to provide an improved liquid infuser apparatus.

In accordance with a primary aspect of the present invention, a liquid infuser apparatus comprises an elastic reservoir comprising an elastic sleeve mounted on a substantially cylindrical support member mounted within a spherical chamber of a collapsible housing.

Another aspect of the invention includes a protective rigid outer housing in which the infuser apparatus may be removeably placed either in the filled or unfilled condition.

A further aspect of the invention comprises a kit of a plurality of the infusers packaged with a single reusable protective rigid outer housing in a compact arrangement.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
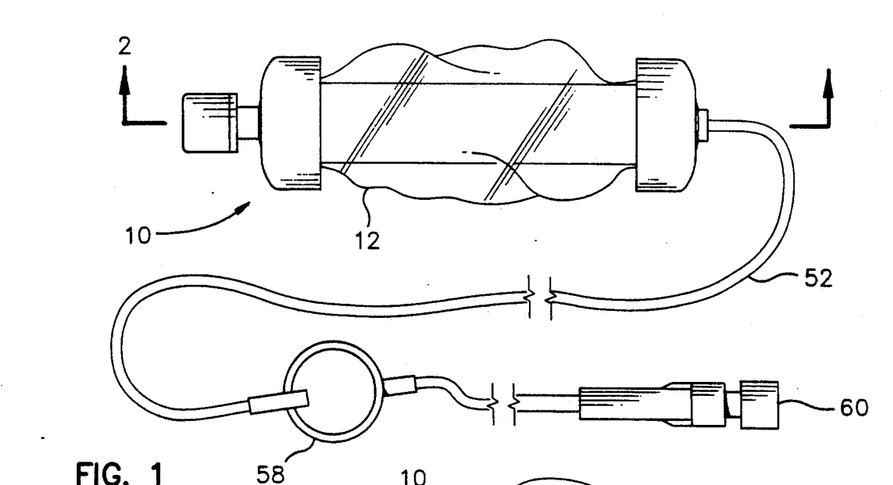
FIG. 1 is a top plan view of a preferred embodiment of the invention.
Figure 2:
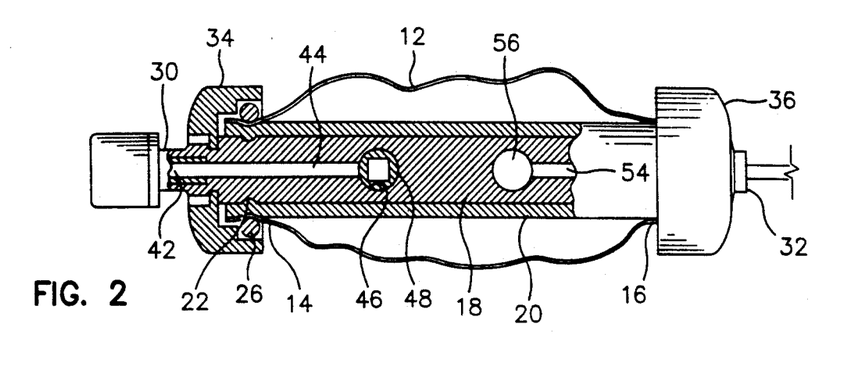
FIG. 2 is a view taken on line 2—2 of FIG. 1.

Referring to the drawings, and particularly to FIGS. 1 and 2, there is illustrated an exemplary embodiment of an infuser pump in accordance with the invention. The infuser pump, designated generally by the numeral 10, is collapsible and comprises an outer collapsible substantially non-stretchable housing or shell 12, protectively mounted over a combined reservoir and support assembly constructed substantially like that set forth in U.S. Pat. Nos. 5,080,652, dated Jan. 14, 1992 and 5,105,983, dated Apr. 21, 1992, both of which are incorporated herein by reference as though fully set forth.

The collapsible housing 12 has a substantially spherical configuration for confining and guiding the inflatable reservoir or bladder into a concentric position around the central support member, and enabling it to expand naturally in a spherical configuration as will be described. The collapsible housing 12, as been seen in FIG. 2, has coaxial openings defined by tubular sleeve extensions 14 and 16 through which the ends of a central support member 18 extends.

An elastic membrane or bladder assembly 20 forming an inflatable reservoir, such as described in the aforementioned patents, is mounted on the cylindrical support member 18. The bladder assembly 20 may be a single sleeve or multiple sleeves, as set forth in the prior patents. This is preferably with an inner sleeve being a chemically inert sleeve, and the outer sleeve or sleeves being highly elastic.

The central cylindrical support member or mandrel 18 includes circular grooves only one of which, 22 is shown, at the ends thereof into which portions of the sleeve 20 and housing 12 are biased by means of a pair of O-rings, only one of which, 26, is shown. The collapsible housing 12 is preferably a non-stretch blow molded housing of from five to ten mils. in thickness and made of a material such as polyurethane, PVC film, and/or polyethylene and is transparent. This forms a simple inexpensive compact unit with a certain amount of protection for the elastic reservoir.

Certain applications may require a tougher collapsible housing. In such cases, the housing should be transparent, UV stable, flexible and highly resistant to puncturing. The housing would be constructed of a material such as tough composites in a flexible form such as a fabric. Examples of such material are available under the trademark Kevelar.

Figure 3:
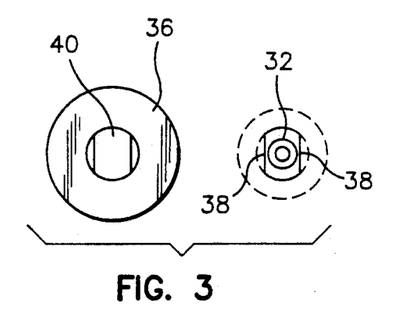
FIG. 3 is an enlarged detailed view of a portion of FIG. 2 showing the retaining cap and coupling.

The ends of the central support member 18 include reduced diameter extension 30 and 32, with bayonette type couplings for releasably coupling cup-shaped caps 34 and 36 which extend over and protectively cover the O-ring connections or clamping of the elastic bladder and collapsible housing to the support member. Referring to FIG. 3, the bayonette connection for member 32 and 36 is illustrated. The member 32 has flat sides 38 for receiving a similarly shaped opening 40 in cap 36, with the cap 36 having inwardly extending flanges forming the flat sides which extend behind shoulders of the extension 32 for retaining the cap in place upon rotation of the cap ninety degrees relative to the member 32. This forms a quick and easy assembly construction for the protective cap.

Figures 4, 5:
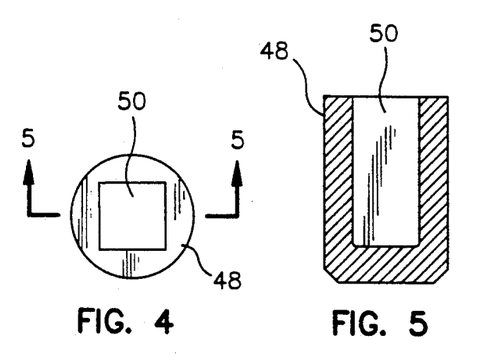
FIG. 4 is an enlarged detailed top view of the check valve assembly of the embodiment of FIG. 1.
FIG. 5 is a section view taken on line 5—5 of FIG. 4.

The support member 18 has an inlet or fill port 42 on one end which communicates with a coaxial passage 44, and a transverse passage 46 in which is mounted a check valve 48. The cross bore 46 communicates with passage 44 and inlet port with the interior of the elastic bladder or sleeve 20 and thus the interior of the inflatable reservoir. The check valve 48 (FIGS. 4 and 5) is of a generally cylindrical outer shape, with a square bore 50 extending from one end and closed at the other forming a cup-shaped structure. The check valve is constructed of an elastomer, such as silicone, and collapses inward to allow filling and erects to its normal configuration to prevent back flow. The square bore configuration of the bore insures that it returns to its normal configuration and does not remain collapsed.

An outlet port through end 32 communicates with a passage 54 that extends coaxially from the other end of the support member 18, and communicates with a cross bore or port 56 with the interior of the elastic bladder or reservoir 20. A tubing set, including a tube 52 having a filter 58 and a connector 60 at the end, provides a means for connecting and dispensing a fluid to a site, such as a vein of a patient.

The collapsible infuser apparatus of FIGS. 1 and 2 comprises a compact and inexpensive disposable unit. It has a compact configuration, with a collapsed diameter no greater than the outer diameter of the caps 34 and 36. For this reason, it is convenient to package in multiple unit kits as will be subsequently described. In addition, it may be temporarily housed during use in a protective hard shell housing as illustrated in FIG. 6.

Figure 6:
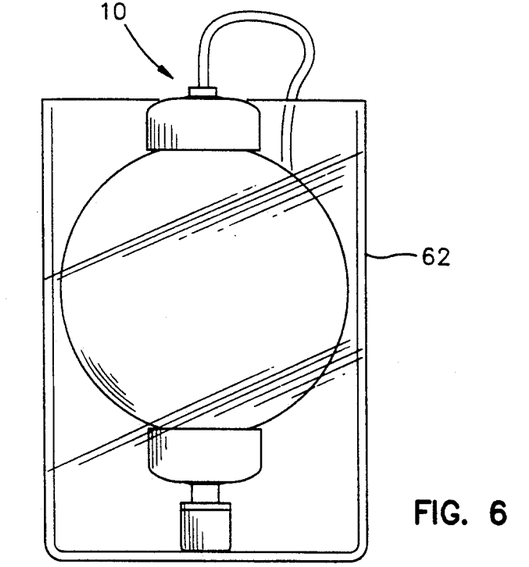
FIG. 6 is a side elevation view showing a filled infuser in a rigid housing.

Referring to FIG. 6, a simple exemplary protective housing 62, in the illustrated embodiment, having a generally cylindrical configuration with an open top and a diameter, can receive and accommodate the fully expanded or filled reservoir during use. This provides a reusable protective housing that may be provided with a kit of multiple infuser units. The protective housing is preferably formed of a high strength material such as polycarbonate. The filled infuser may be placed in the protective housing 62 and placed in a carrying pouch, thereby providing protection against accidental undue pressure or accidental puncturing of the reservoir bladder. The inflatable bladder or reservoir is very susceptible to puncturing when in the inflated condition. For this reason, it is desirable that it be within a puncture resistive housing when inflated. The housing 62 may have other configurations and may have a removable cover if desired (see FIGS. 11 and 12).

Figure 7:
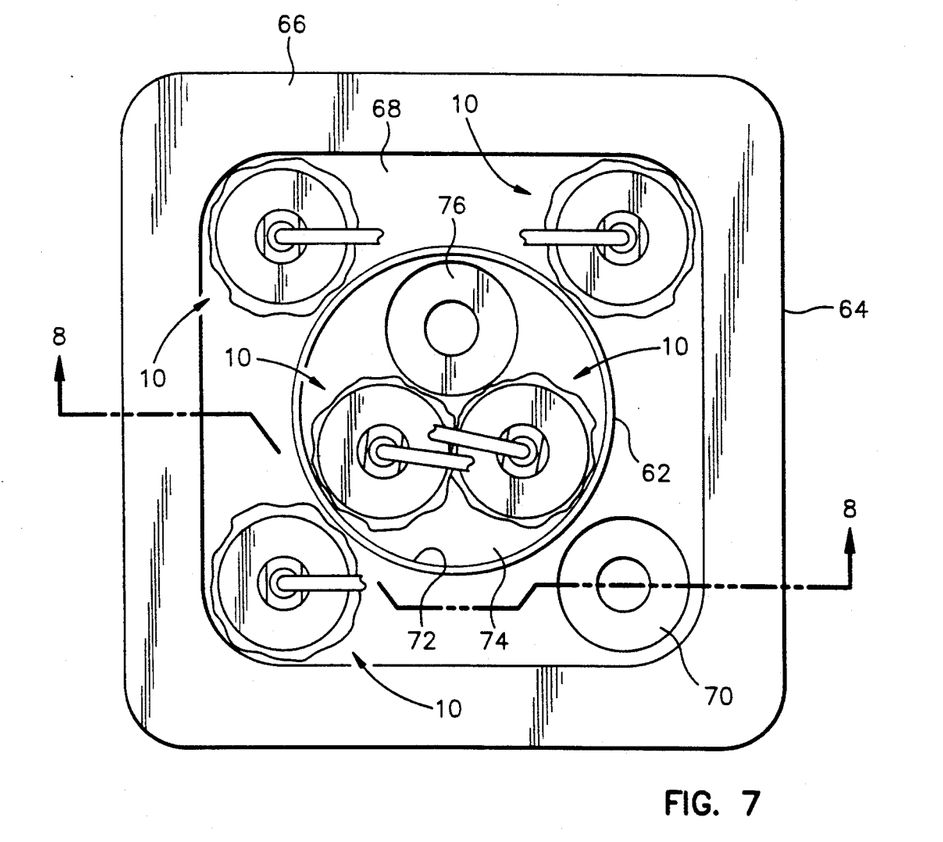
FIG. 7 is a top plan view of a kit embodiment of the invention.
Figure 8:
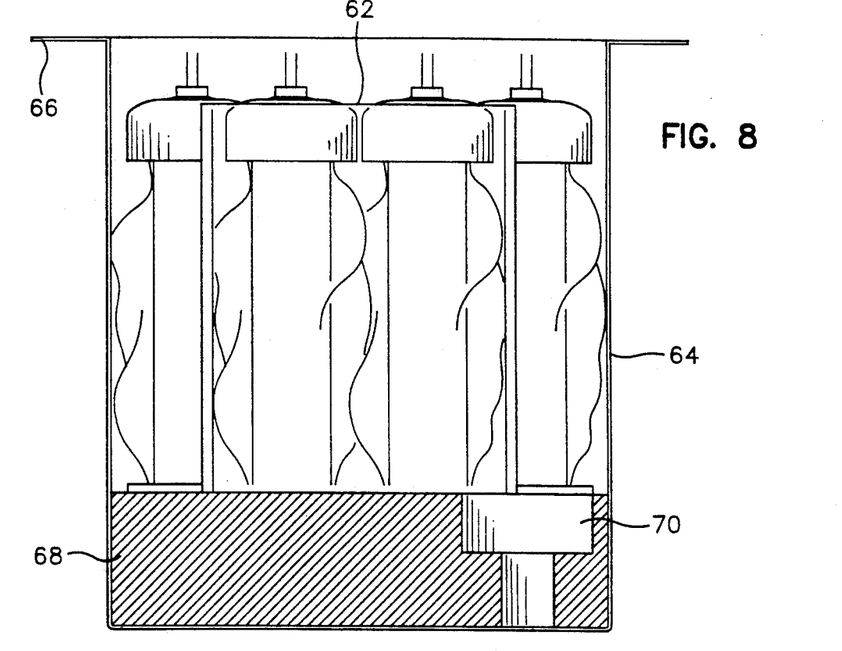
FIG. 8 is a section view taken generally on lines 8—8 of FIG. 7.

Referring to FIGS. 7 and 8, a kit of multiple infusers, in accordance with the invention, is packaged as a kit for convenient use for a seven day period, for example. As illustrated in FIGS. 7 and 8, the kit comprises a generally rectangular opened top box or container 64 of a very thin, substantially rigid plastic material having a peripheral flange 66 for attachment of a suitable cover. The container forms a chamber in which is placed a styrofoam support block 68 having a plurality of bores 70 spaced around the periphery thereof for receiving the inlet end and cap portion of a plurality of the infusers 10.

A cylindrical bore 72 in the center of the block 68 receives the cylindrical housing 62 in an upright position. Positioned within the housing 62 is a circular or cylindrical styrofoam block 74 having three bores 76 similar to the bore 70 for receiving the filler ends of three infusers 10. This provides a kit of seven infuser units providing a week's supply.

These kits are easily packaged at a factory and shipped to a hospital or to a pharmacist who removes and fills the infusers and supplies them along with a reusable housing 68 to a patient for home use. The patient then uses each of the infusers in consecutive order and disposes of them when used. This provides a compact convenient package. The package has a typical size of approximately 4 ¼ inches high and 3¾ inches on a side. This takes up slightly more than the space of a single unit of the prior design having a hard shell. For example, a one-hundred milliliter hard shell unit is about 4 inches in length and about 2½ to 3 inches in diameter. Thus, a package of seven of the present units takes about sixteen cubic inches of space versus about twelve cubic inches for one of the prior units.

Figure 9:
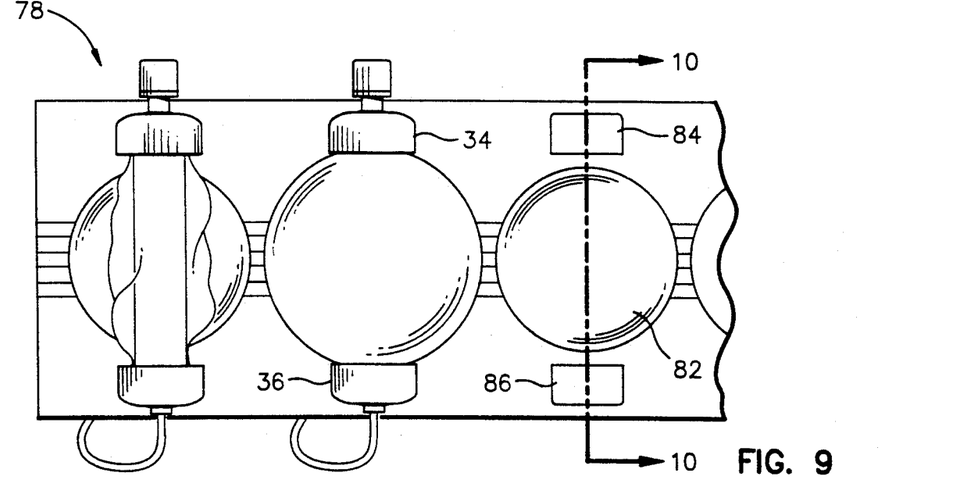
FIG. 9 is a top plan view of a filling jig for use with the invention.
Figure 10:
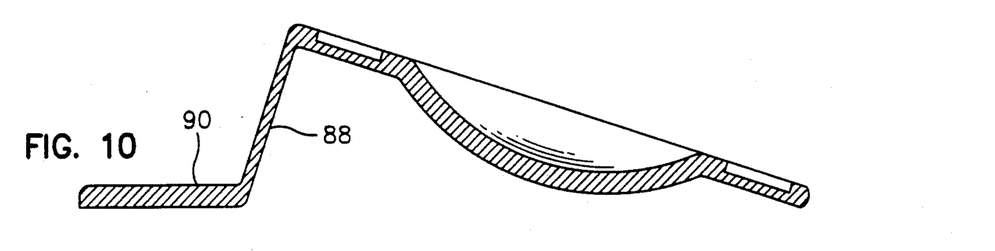
FIG. 10 is a section view taken generally on lines 10—10 of FIG. 9.

Referring to FIGS. 9 and 10, a convenient filling rack for an infuser of the present design is illustrated, designated generally by the numeral 78. The rack is molded of a suitable plastic material and is formed within the illustrated embodiment with 7 (or any other suitable number) identical holder positions. Each holder position has a central cavity 82 for receiving and enabling expansion of the bladder, an upper recess 84 for receiving a filler end cap 34, and a lower recess 86 for receiving a cap 36. The panel 80 has a forward leg 88, with a foot 90 to hold the support panel in an included position for ease of use. The pharmacist may simply load the rack with a plurality of infusers and either fill them in sequence or simultaneously as desired.

Figure 11:
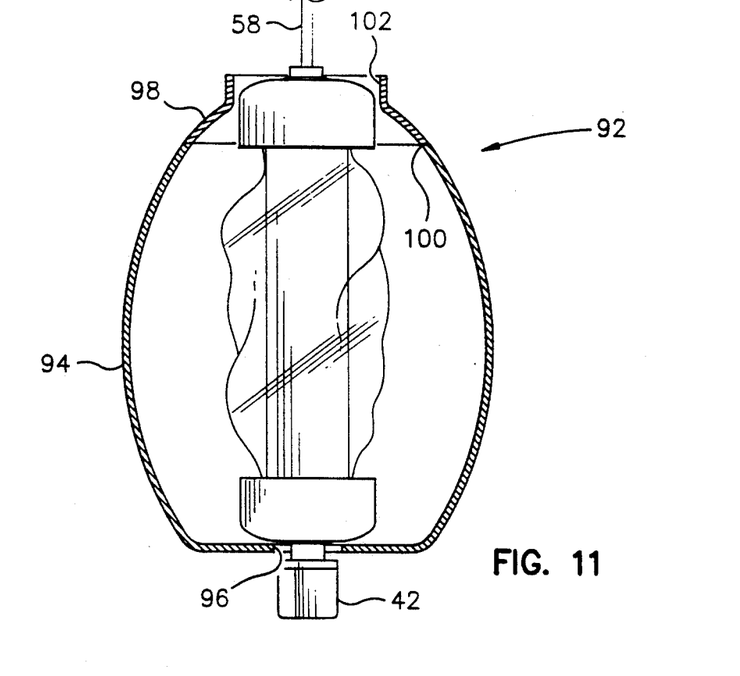
FIG. 11 is a side elevation view of an alternate embodiment of a rigid housing.

Referring now to FIG. 11, an alternate embodiment of an outer housing or shell is illustrated and designated generally by the numeral 92. This outer housing has a somewhat spherical configuration with outer spherical walls 94 and a lower end which may have an opening 96 for exposing an inlet or fill port 42 for filling. A removable cap 98 provides a closure for an opening 100 in the top of the housing. The cap includes a central opening 102 for extension of a tubing set 58. The cap 98 may be attached in any suitable manner such as friction fit, bayonette type coupling, threads or the like to the housing.

The opening 100 in the upper end of the housing walls may be sufficiently large to enable a filled infuser unit, as disclosed in FIGS. 1 and 2, to be inserted into the housing. This provides a reusable housing which may also include a cap or closure for protectively closing the unit. In addition, this provides a housing in which the unit without a protective collapsible housing may also be enclosed or housed for filling. In other words, with this unit the collapsible housing 12 of the FIGS. 1 and 2 unit may be eliminated. This provides an alternate compact arrangement wherein multiple compact units may be packaged with a single protective outer housing, and provided to a pharmacist for filling and supplying to patients.

Figure 12:
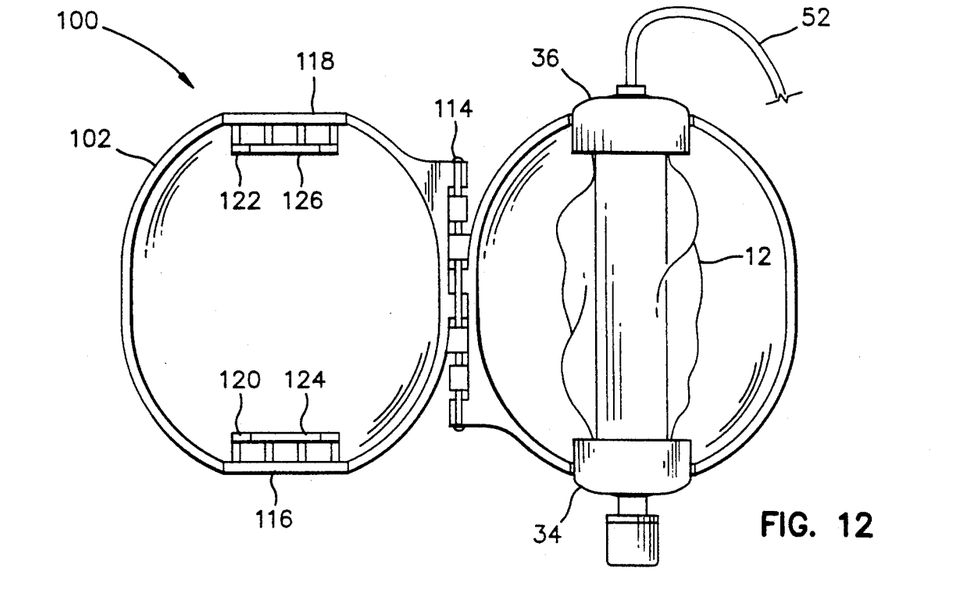
FIG. 12 is a side elevation view of a further embodiment of a rigid housing.

Referring to FIG. 12, an openable spherical shell embodiment of a protective housing is illustrated and designated generally at 100. The housing is constructed of two identical half-shells 102 connected together by a hinge pin 114. Thus, a filled or unfilled infuser may be placed in the reusable protective housing. The shells each have an opening 116 and 118 at each end with an inwardly spaced wall 120 and 122, each having an opening 124 and 126. The end caps 34 and 36 of an infuser are received in the openings 116 and 118, and the central support member 18 is received in the openings 124 and 126. The ends of the infuser unit are thereby exposed for access. The hinge axis extends along a line parallel to an axis defined by the openings in the shell.

Figure 13:
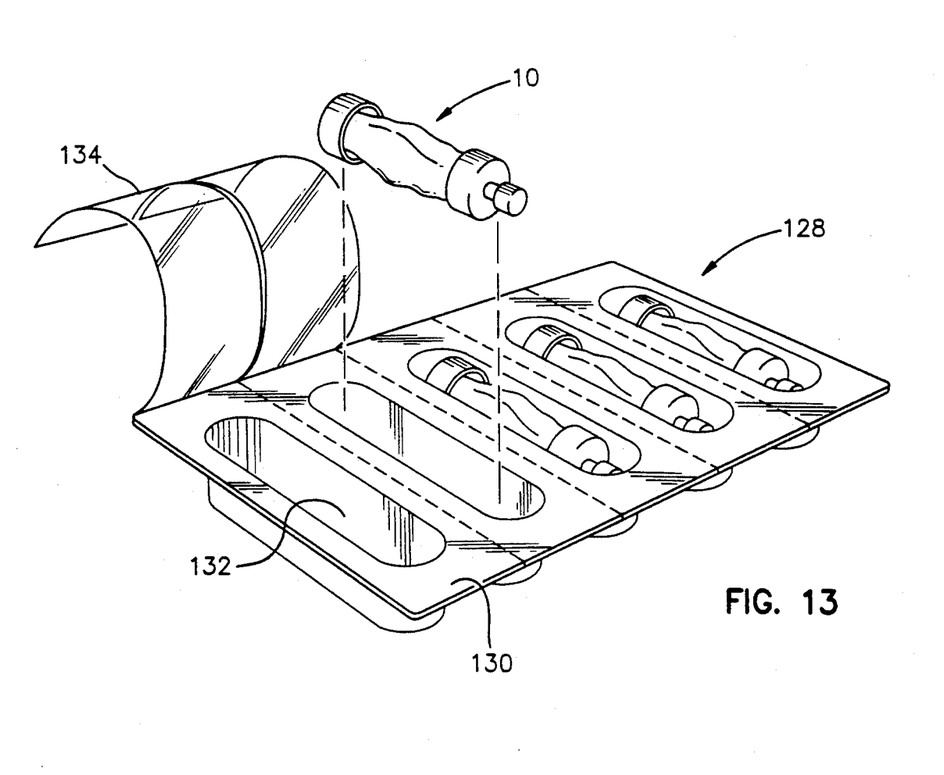
FIG. 13 is a perspective view of an alternate shipping package embodiment of the invention.

Referring to FIG. 13, an alternate embodiment of a packaging system for multiple infusers is illustrated and designated generally by the numeral 128. A base container sheet 130 has a plurality of cavities 132 formed therein for receiving infuser units 10. A cover sheet 134 covers the base sheet and cavities to protectively seal the infuser units in the cavities. The base sheet may be either flexible or somewhat rigid. The base sheet and cover sheet have perforations 136 separating the cavities 132. This enables selective separation of single units from the overall package. Alternatively, the entire cover sheet can be peeled away to provide common access to a plurality of the infuser units.

Figure 14:
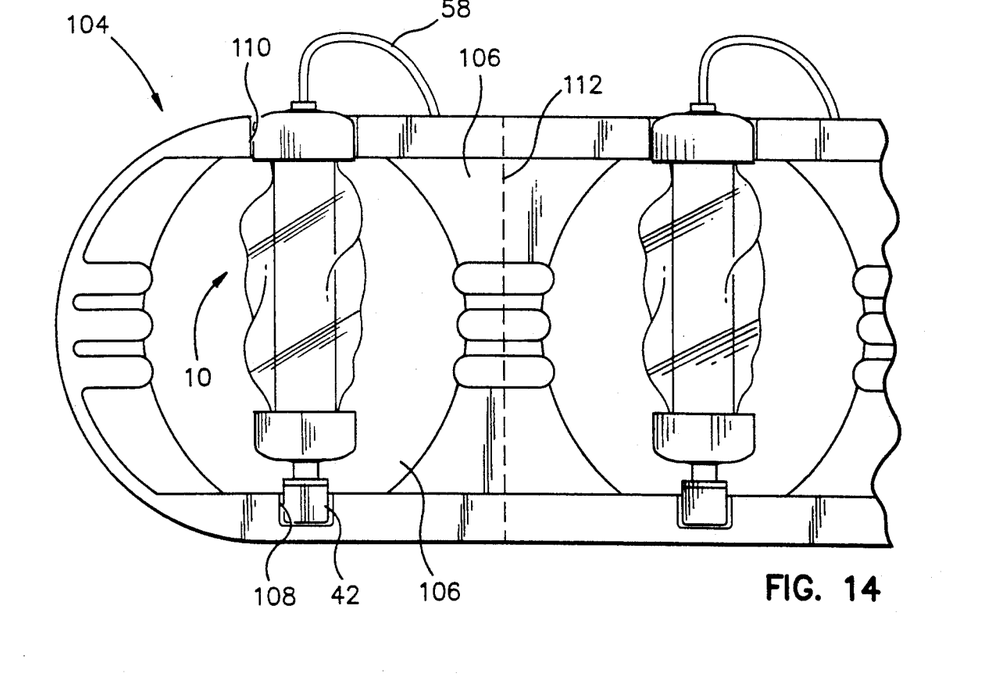
FIG. 14 is a top plan view of a combined package and rigid housing embodiment of the invention.

Referring to FIG. 14, an alternate embodiment of combined packaging and protective housing is illustrated. This package, designated generally by the numeral 104, comprises opposed thin plastic sheets, only one of which 106 is shown, forming mirror images of one another. These opposed sheets have semi-spherical recesses or cavities forming a generally spherical chamber in which a dispensing unit 10, substantially as described in FIGS. 1 and 2, is encapsulated, with an opening or bore 108 through which a filler port or cap 42 extends. The package also provides an opening 110 at the other end for extension of a tubing set 58. The entire package can contain any selected number of units which may be shipped to a pharmacist. The pharmacist may take the package and select and separate an appropriate number of the infusers, fill them and supply them to a patient. The infuser units may be separated along a perforated line 112 of the package such that an individual infuser may be separated from the remainder.

Thus, the unit of FIG. 1 can be effectively packaged in simple and inexpensive packaging for supplying to pharmacists. This form of packaging can also be used without the collapsible housing, such that the unit contains only the inflatable reservoir, and the packaging forms a protective non-collapsible housing. Similarly, the units without the collapsible housing can be used with any of the rigid housings discussed herein.

While we have illustrated and described our invention by means of specific embodiments, it is to be understood that numerous changes and modifications may be made therein without departing from the spirit and scope of the invention as defined in the appended claims.

We claim:

1. A compact portable apparatus for dispensing a liquid under pressure at a substantially constant flow rate over a period of time comprising:

an elongated generally cylindrical support member;

elongated elastic sleeve means mounted and sealingly secured at fixed spaced longitudinal positions on said support member for defining a substantially zero non-pressurized volume pressure reservoir for holding a liquid in a pressurized state for dispensing therefrom;

housing means comprising collapsible non-stretchable housing means for containing said support member and said pressure reservoir for enabling said pressure reservoir to expand naturally and for confining said reservoir to fill concentrically about said support member;

inlet means for introducing a liquid into said elastic pressure reservoir; and outlet means for dispensing liquid from said pressure reservoir to a selected site.

2. An apparatus for dispensing a liquid under pressure according to claim 1 wherein said collapsible non-stretchable housing means comprises a substantially spherical housing.

3. An apparatus for dispensing a liquid under pressure according to claim 2 wherein said housing means further comprises a generally cylindrical substantially rigid housing having an open end for receiving said support member.

4. An apparatus for dispensing a liquid under pressure according to claim 2 wherein:

said support member is an elongated generally cylindrical mandrel mounted in said housing means and having opposite ends exposed to the exterior of said housing means, said inlet means comprises an inlet port in one end of said mandrel, and said outlet means comprises an outlet port in the other end of said mandrel; and said housing means is clamped at opposite ends thereof with said elastic sleeve means around opposite ends of said mandrel by an elastic ring.

5. An apparatus for dispensing a liquid under pressure according to claim 1 wherein:

said collapsible non-stretchable housing means is substantially spherical having openings formed in opposite ends thereof by co-extending tubular sleeves; and said housing means is commonly clamped at opposite ends thereof with said elastic sleeve means around opposite ends of said support member by means of an O-ring extending around said tubular sleeves.

6. An apparatus for dispensing a liquid under pressure according to claim 5 wherein said said O-rings are each covered by a cup shaped cap removeably attached to the ends of said support member.

7. An apparatus for dispensing a liquid under pressure according to claim 6 wherein said housing means further comprises a generally cylindrical substantially rigid housing having an open end for receiving said support member coaxially therein.

8. An apparatus for dispensing liquid under pressure according to claim 6 wherein said housing means comprises a substantially spherical rigid housing formed of like half-shells hinged together for removably receiving said support member and elastic sleeve.

9. An apparatus for dispensing liquid under pressure according to claim 8 wherein said housing has openings forming stepped recesses for receiving said caps.

10. An apparatus for dispensing a liquid under pressure according to claim 1 wherein:
said housing means comprises a flexible non-stretchable shell having a substantially spherical central chamber with openings formed in opposite ends thereof by co-extending tubular sleeves; and
said housing means is secured at opposite ends thereof with said elastic sleeve means around opposite ends of said support member by means of an O-ring extending around said tubular sleeves.

11. An apparatus for dispensing a liquid under pressure according to claim 10 wherein said said O-rings are each covered by a cup shaped cap removeably attached to the ends of said support member.

12. An apparatus for dispensing a liquid under pressure according to claim 1 wherein said housing means comprises a substantially rigid housing having an opening in one end for receiving said support member coaxially therein.

13. An apparatus for dispensing a liquid under pressure according to claim 12 wherein said rigid housing has a substantially spherical configuration with a removable closure for enabling receipt of said pressure reservoir in a filled condition.

14. An apparatus for dispensing liquid under pressure according to claim 1 wherein said housing means comprises a substantially shperical rigid housing formed of like half-shells hinged together.

15. A compact collapsible infusion apparatus for dispensing a liquid under pressure at a predetermined substantially constant flow rate over a period of time comprising:
an elongated generally cylindrical support member having inlet means including an inlet port in one end of said member, and outlet means including an outlet port in the other end of said member;
elongated elastic sleeve means mounted in non-stretched surface contact and sealingly secured at fixed spaced longitudinal positions on said support member for defining a substantially zero non-pressurized volume pressure reservoir for holding a liquid in a pressurized state for dispensing therefrom;
first housing means including a collapsible shell enclosing said support member and said pressure reservoir, said housing having a size and shape for enabling said pressure reservoir to expand naturally and for confining said reservoir to fill concentrically about said support member;
inlet means in one end of said support member for introducing a liquid into said elastic pressure reservoir; and outlet means in the other end of said support member for dispensing liquid from said pressure reservoir to a selected site.

16. An apparatus for dispensing a liquid under pressure according to claim 15 wherein:
said housing means comprises a flexible non-stretchable shell having a substantially spherical central chamber with openings formed in opposite ends thereof by co-extending tubular sleeves; and
said housing means is secured at opposite ends thereof with said elastic sleeve means around opposite ends of said support member by means of an O-ring extending around said tubular sleeves.

17. An apparatus for dispensing a liquid under pressure according to claim 16 wherein said housing means further comprises a generally cylindrical substantially rigid housing having an open end for receiving said support member coaxially therein.

18. Apparatus for dispensing a liquid under pressure according to claim 16 further comprising a cup shaped cap removeably attached to each end of said support member for protectively covering said O-rings.

19. An apparatus for dispensing a liquid under pressure according to claim 18 wherein said housing means comprises a substantially rigid housing having an opening in one end for receiving said support member coaxially therein.

20. An apparatus for dispensing liquid under pressure according to claim 16 wherein said housing means further comprises a pair of substantially semi-spherical pivotably connected half-shells forming a substantially spherical rigid housing.

21. An apparatus for dispensing liquid under pressure according to claim 20 wherein said housing has openings forming stepped recesses for receiving said caps.

22. An apparatus for dispensing liquid under pressure according to claim 20 wherein said housing has openings forming stepped recesses for receiving said caps.

23. A medical infusion kit having multiple apparatus for dispensing multiple dosages of a liquid under pressure at a substantially constant flow rate over a period of time comprising:
a plurality of substantially identical collapsible infusion devices, each having a collapsible housing having a chamber for containing a pressure reservoir, an elongated generally cylindrical support member disposed in and extending through said chamber, an expansible elastic pressure reservoir mounted on said support member in said chamber for holding said liquid under pressure during dispensing thereof, said elastic pressure reservoir comprises an elastic sleeve snugly mounted over said support member in said chamber for defining a pressure reservoir for holding a liquid in a pressurized state for dispensing therefrom, inlet means in one end of said support member for introducing a liquid into said elastic sleeve;
a substantially rigid housing having an open end for removeably receiving said infusion devices coaxially therein in a filled condition; and
outlet means in the other end of said support member for conveying a liquid from said pressure reservoir to a selected site.

24. An infusion kit according to claim 23 wherein said collapsible housing comprises a flexible non-stretchable shell having a substantially spherical central chamber with openings formed in opposite ends thereof by co-extending tubular sleeves; and said shell is secured at opposite ends thereof with said elastic sleeve around opposite ends of said support member by means of an O-ring extending around said tubular sleeves.

25. An infusion kit according to claim 24 further comprising a cup shaped cap removeably attached to each end of said support member for protectively covering said O-rings.

26. An infusion kit according to claim 25 wherein wherein said plurality of infusion devices are from five to seven in number.

27. A compact portable dispensing apparatus for dispensing a liquid under pressure at a substantially constant flow rate over a period of time comprising:
- an elongated substantially cylindrical support member;
- elongated elastic sleeve means mounted on and sealingly secured at fixed spaced longitudinal positions on said support member for defining a pressure reservoir for holding a liquid in a pressurized state for dispensing therefrom;
- housing means comprising a substantially spherical rigid housing formed of like half-shells hinged together for removeably containing said support member and said pressure reservoir for enabling said pressure reservoir to expand naturally and for confining said reservoir to fill concentrically about said support member;
- inlet means for introducing a liquid into said elastic pressure reservoir; and
- outlet means for dispensing liquid from said pressure reservoir to a selected site.

28. An apparatus for dispensing a liquid under pressure according to claim 27 wherein:
- said housing means comprises a flexible non-stretchable shell having a substantially spherical central chamber with openings formed in opposite ends thereof by co-extending tubular sleeves; and
- said housing means is secured at opposite ends thereof with said elastic sleeve means around opposite ends of said support member by means of an O-ring extending around said tubular sleeves.

* * * * *

(12) EX PARTE REEXAMINATION CERTIFICATE (6926th)
United States Patent
Soika et al.

(10) Number: US 5,284,481 C1
(45) Certificate Issued: Jul. 14, 2009

(54) COMPACT COLLAPSIBLE INFUSION APPARATUS

(75) Inventors: Emil H. Soika, Poway, CA (US); Steven R. Payne, San Diego, CA (US)

(73) Assignee: I-Flow Corporation, Lake Forest, CA (US)

Reexamination Request:
No. 90/008,880, Nov. 12, 2007

Reexamination Certificate for:
Patent No.: 5,284,481
Issued: Feb. 8, 1994
Appl. No.: 07/984,899
Filed: Dec. 2, 1992

(51) Int. Cl.
*A61M 37/00* (2006.01)
*A61M 5/145* (2006.01)
*A61M 5/152* (2006.01)

(52) U.S. Cl. .................. 604/132; 206/438; 206/370; 222/105

(58) Field of Classification Search .................. None
See application file for complete search history.

(56) References Cited

U.S. PATENT DOCUMENTS

| | | | |
|---|---|---|---|
| 3,215,299 | A | 11/1965 | Coanda et al. |
| 3,810,503 | A | 5/1974 | Lewis, Jr. et al. |
| 4,010,783 | A | 3/1977 | Ralston |
| 4,386,929 | A | 6/1983 | Peery et al. |
| 4,522,302 | A * | 6/1985 | Paikoff .................. 206/570 |
| 4,539,005 | A | 9/1985 | Greenblatt |
| 4,547,900 | A | 10/1985 | Larkin et al. |
| 4,573,992 | A | 3/1986 | Marx |
| 4,686,125 | A | 8/1987 | Johnston et al. |
| 4,828,892 | A | 5/1989 | Kersten et al. |
| 5,080,652 | A | 1/1992 | Sancoff et al. |
| 5,105,983 | A | 4/1992 | Sancoff et al. |
| 5,135,497 | A | 8/1992 | Hessel et al. |
| 5,263,940 | A | 11/1993 | Kriesel |
| 5,284,481 | A | 2/1994 | Soika et al. |

FOREIGN PATENT DOCUMENTS

| | | |
|---|---|---|
| EP | 90311152.4 | 10/1990 |
| WO | WO 88/03819 | 6/1988 |

OTHER PUBLICATIONS

*I-Flow Corporation v. AIM Enterprises, Inc.;* U.S. District Court District of Arizona (Phoenix Division) Civil Docket for Case #: 2:08–cv–01659–GMS; pp. 1–4.

*I-Flow Corporation v. Alpin Surgical Specialties, Inc.;* U.S. District Court Western District of Pennsylvania (Pittsburgh) Civil Docket for Case #: 2:08–cv–01232–DWA; pp. 1–5.

*I-Flow Corporation v. Apex Medical Technologies, Inc.;* U.S. District Court Southern District of California (San Diego) Civil Docket for Case #: 3:07–cv–01200–DMS–NLS; pp. 1–13.

*I-Flow Corporation v. Biomet Texas, Inc.;* U.S. District Court Northern District of Texas (Dallas) Civil Docket for Case #: 3:08–cv–01602–O; pp. 1–2.

*I-Flow Corporation v. West Coast Aesthetics et al.;* United States District Court, Central District of California (Southern Division—Santa Ana) Civil Docket for Case #: 8:08–cv–00784–AG–RNB; pp. 1–5.

*I-Flow Corporation v. Zone Medical, LLC;* U.S. District Court Southern District of California (San Diego) Civil Docket for Case #: 3:08–cv–00057–DMS–NLS; pp. 1–3.

*I-Flow Corporation v. Apex Medical Technologies, Inc.;* United States District Court Southern District of California; Case No. 07–CV–1200–DMS(NLS); Defendants' Motion For Leave To Amend Their Final Invalidity Contentions.

(Continued)

*Primary Examiner*—Catherine S. Williams (57) ABSTRACT

A liquid infuser apparatus includes an elastic sleeve mounted on an elongated member and within a collapsible spherical housing to enable it to expand naturally to maintain a constant pressure over the infusion period. A rigid open ended housing into which an infuser may be removeably placed provides a reusable protective housing. Multiple infusers are packaged with a rigid housing in a kit.

OTHER PUBLICATIONS

*I–Flow Corporation* v. *Apex Medical Technologies, Inc.;* United States District Court Southern District of California; Case No. 07–CV–1200–DMS(NLS); Plaintiff's Opposition to Defendants' Motion For Leave To Amend Their Final Invalidity Contentions.

*I–Flow Corporation* v. *Apex Medical Technologies, Inc.;* United States District Court Southern District of California; Case No. 07–CV–1200–DMS(NLS); Reply to I–Flow's Opposition to Defendants' Motion For Leave To Amend Their Final Invalidity Contentions.

*I–Flow Corporation* v. *Apex Medical Technologies, Inc.;* United States District Court Southern District of California; Case No. 07–CV–1200–DMS(NLS); Order Granting Defendants' Motion For Leave To Amend Their Final Invalidity Contentions.

*I–Flow Corp.* v. *Apex Medical Technologies, Inc.,* Case No. 07–cv–1200 DMS (NLS): I–Flow's Opposition to Defendants' Motion for Summary Judgment of Invalidity.

*I–Flow Corp.* v. *Apex Medical Technologies, Inc.,* Case No. 07–cv–1200 DMS (NLS): I–Flow's Objections to Certain Evidence Offered by Defendants in Support of Their Motion for Summary Judgment.

*I–Flow Corp.* v. *Apex Medical Technologies, Inc.,* Case No. 07–cv–1200 DMS (NLS): Declaration of Boris Zelkind in Opposition to Defendants' Motion for Summary Judgment of Invalidity ("Zelkind Declaration").

*I–Flow Corp.* v. *Apex Medical Technologies, Inc.,* Case No. 07–cv–1200 DMS (NLS): Declaration of Roger Massengale in Opposition to Defendants' Motion for Summary Judgment of Invalidity ("Massengale Declaration").

*I–Flow Corp.* v. *Apex Medical Technologies, Inc.,* Case No. 07–cv–1200 DMS (NLS): Declaration of Gary L. Loomis in Opposition to Defendants' Motion for Summary Judgment of Invalidity ("Loomis Declaration").

*I–Flow Corp.* v. *Apex Medical Technologies, Inc.,* Case No. 07–cv–1200 DMS (NLS): Declaration of Len Czuba in Opposition to Defendants' Motion for Summary Judgment of Invalidity ("Czuba Declaration").

*I–Flow Corp.* v. *Apex Medical Technologies, Inc.,* Case No. 07–cv–1200 DMS (NLS): Exhibit 4 to Zelkind Declaration: Rule 97 Disclosure Statement for U.S. Appl. No. 07/984, 899.

*I–Flow Corp.* v. *Apex Medical Technologies, Inc.,* Case No. 07–cv–1200 DMS (NLS): Exhibit 5 to Zelkind Declaration: Response to Office Action in Ex Parte Reexamination for Control No. 90/008,880.

*I–Flow Corp.* v. *Apex Medical Technologies, Inc.,* Case No. 07–cv–1200 DMS (NLS): Exhibit 6 to Zelkind Declaration: Excerpts of a deposition of Apr. 18, 2008, of Stephen Hessel.

*I–Flow Corp.* v. *Apex Medical Technologies, Inc.,* Case No. 07–cv–1200 DMS (NLS): Exhibit 7 to Zelkind Declaration: Declaration / Power of Attorney for Original Application.

*I–Flow Corp.* v. *Apex Medical Technologies, Inc.,* Case No. 07–cv–1200 DMS (NLS): Reply in Support of Defendants' Motion for Summary Judgment of Invalidity under 35 U.S.C. §§ 102(b) and 103(a) of Claims 1, 2 and 15 of U.S. Patent No. 5,284,481.

*I–Flow Corp.* v. *Apex Medical Technologies, Inc.,* Case No. 07–cv–1200 DMS (NLS): Defendants' Objections to Expert Declarations Submitted with I–Flow's Opposition to Motion for Summary Judgment of Invalidity under 35 U.S.C. §§ 102(b) and 103(a) of Claims 1, 2 and 15 of U.S. Patent No. 5,284,481.

*I–Flow Corp.* v. *Apex Medical Technologies, Inc.,* Case No. 07–cv–1200 DMS (NLS): Defendants' Motion for Summary Judgment of Invalidity under 35 U.S.C. §§ 102(b) and 103(a) of Claims 1, 2 and 15 of U.S. Patent No. 5,284,481.

*I–Flow Corp.* v. *Apex Medical Technologies, Inc.,* Case No. 07–cv–1200 DMS (NLS): Memorandum of Points and Authorities in Support of Defendants' Motion for Summary Judgment of Invalidity under 35 U.S.C. §§ 102(b) and 103(a) of Claims 1, 2 and 15 of U.S. Patent No. 5,284,481.

*I–Flow Corp.* v. *Apex Medical Technologies, Inc.,* Case No. 07–cv–1200 DMS (NLS): Declaration of Norbert Stahl in Support of Defendants' Motion for Summary Judgment of Invalidity under 35 U.S.C. §§ 102(b) and 103(a) of Claims 1, 2 and 15 of U.S. Patent No. 5,284,481 ("Stahl Declaration").

*I–Flow Corp.* v. *Apex Medical Technologies, Inc.,* Case No. 07–cv–1200 DMS (NLS): Exhibit C to Stahl Declaration: Office Action in Reexamination Control No. 90/008,880.

*I–Flow Corp.* v. *Apex Medical Technologies, Inc.,* Case No. 07–cv–1200 DMS (NLS): Exhibit D to Stahl Declaration: Interview Summary in Reexamination Control No. 90/008, 880.

*I–Flow Corp.* v. *Apex Medical Technologies, Inc.,* Case No. 07–cv–1200 DMS (NLS): Exhibit E to Stahl Declaration: Response to Office Action in Ex Parte Reexamination in Reexamination Control No. 90/008,880.

*I–Flow Corp.* v. *Apex Medical Technologies, Inc.,* Case No. 07–cv–1200 DMS (NLS): Exhibit F to Stahl Declaration: Excerpts of a deposition of Dec. 3, 2008, of Emil Soika.

*I–Flow Corp.* v. *Apex Medical Technologies, Inc.,* Case No. 07–cv–1200 DMS (NLS): Exhibit G to Stahl Declaration: Defendants' Amended Final Invalidity Contentions.

*I–Flow Corp.* v. *Apex Medical Technologies, Inc.,* Case No. 07–cv–1200 DMS (NLS): Exhibit O to Stahl Declaration: letters of Knobbe Martens Olson & Bear LLP to Karma D Medical, New Mexico, dated Oct. 3, 2008, and to Pain Solutions Partner, Kentucky, dated Oct. 3, 2008 and Nov. 19, 2008.

*I–Flow Corporation* v. *Apex Medical Technologies, Inc.;* Defendants' Motion for Summary Judgment of Invalidity under 35 U.S.C. §§102(b) and 103(a) of Claims 1, 2 and 15 of U.S. Patent No. 5,284,481; Jan. 8, 2009.

*I–Flow Corporation* v. *Apex Medical Technologies, Inc.;* Memorandum of Points and Authorities in Support of Defendants' Motion for Summary Judgment of Invalidity under 35 U.S.C. §§102(b) and 103(a) of Claims 1, 2 and 15 of U.S. Patent No. 5,284,481; Jan. 8, 2009.

*I–Flow Corporation* v. *Apex Medical Technologies, Inc.;* Declaration of Norbert Stahl in Support of Defendants' Motion for Summary Judgment of Invalidity under 35 U.S.C. §§102(b) and 103(a) of Claims 1, 2 and 15 of U.S. Patent No. 5,284,481; Jan. 8, 2009.

*I–Flow Corporation* v. *Apex Medical Technologies, Inc.;* I–Flow's Opposition to Defendants' Motion for Summary Judgment of Invalidity; Jan. 23, 2009.

*I–Flow Corporation* v. *Apex Medical Technologies, Inc.;* Reply in Support of Defendants' Motion for Summary Judgment of Invalidity under 35 U.S.C. §§102(b) and 103(a) of Claims 1, 2 and 15 of U.S. Patent No. 5,284,481; Jan. 30, 2009.

*I-Flow Corporation* v. *Apex Medical Technologies, Inc.;* Defendants' Answer to Plaintiff's Second Amended Complaint for Patent Infringement, Trade Secret Misappropriation, Breach of Confidence, and Common Law and Statutory Unfair Competition and Counterclaims, 07 CV 1200 DMS (NLS); Apr. 22, 2007.
*I-Flow Corporation* v. *Apex Medical Technologies, Inc.;* Plaintiff's Reply to Defendants' Answer to Second Amended Complaint and Counterclaims, 07 CV 1200 DMS (NLS); May 14, 2008.
*I-Flow Corporation* v. *Apex Medical Technologies, Inc.;* Plaintiff's Claim Construction Opening Brief, 07 CV 1200 DMS (NLS); May 19, 2008.
*I-Flow Corporation* v. *Apex Medical Technologies, Inc.;* Defendants' Claim Construction Opening Brief, 07 CV 1200 DMS (NLS); May 19, 2008.
*I-Flow Corporation* v. *Apex Medical Technologies, Inc.;* Zone Medical, LLC's Answer to Plaintiff's Complaint for Patent Infringement and Counterclaims, 07 CV 1200 DMS (NLS); May 30, 2008.
*I-Flow Corporation* v. *Apex Medical Technologies, Inc.;* Defendants' Claim Construction Reply Brief, 07 CV 1200 DMS (NLS); Jun. 2, 2008.
*I-Flow Corporation* v. *Apex Medical Technologies, Inc.;* I-Flow's Responsive Claim Construction Brief, 07 CV 1200 DMS (NLS); Jun. 2, 2008.
*I-Flow Corporation* v. *Apex Medical Technologies, Inc.;* Plaintiff's Answer to Zone Medical's Counterclaims, 07 CV 1200 DMS (NLS); Jun. 23, 2008.
*I-Flow Corporation* v. *Apex Medical Technologies, Inc.;* Order Construing Patent Claims, 07 CV 1200 DMS (NLS); Jul. 25, 2008.
*I-Flow Corporation* v. *West Coast Aesthetics et al.;* Complaint for Patent Infringement; Trade Secret Misappropriation; Breach of Confidence; Breach of Contract; and Common Law and Statutory Unfair Competition, 08 CV 00784 AG (RNB); Jul. 17, 2008.
*I-Flow Corporation* v. *West Coast Aesthetics et al.;* Defendants' Answer to Plaintiff's Complaint for Patent Infringement; Trade Secret Misappropriation, Breach of Confidence; Breach of Contract; and Common Law and Statutory Unfair Competition and Counterclaims, 08 CV 00784 AG (RNB); Aug. 14, 2008.
*I-Flow Corporation* v. *West Coast Aesthetics et al.;* Defendants' Amended Answer to Plaintiff's Complaint for Patent Infringement; Trade Secret Misappropriation; Breach of Confidence; Breach of Contract; and Common Law and Statutory Unfair Competition and Counterclaims, 08 CV 00784 AG (RNB); Aug. 15, 2008.
*I-Flow Corporation* v. *West Coast Aesthetics et al.;* Defendants' Amended Answer to Plaintiff's Complaint for Patent Infringement; Trade Secret Misappropriation, Breach of Confidence; Breach of Contract; and Common Law and Statutory Unfair Competition and Counterclaims, 08 CV 00784 AG (RNB); Aug. 21, 2008.
*I-Flow Corporation* v. *West Coast Aesthetics et al.;* Plaintiff I-Flow Corporation's Reply to Defendants West Coast Aesthetics and TJK Group, Inc.'s Counterclaims, 08 CV 00784 AG (RNB); Sep. 2, 2008.
*I-Flow Corporation* v. *Alpin Surgical Specialties, Inc.;* Complaint for Patent Infringement and Demand for Jury Trial; 08 CV 01232 (DWA); Sep. 4, 2008.
*I-Flow Corporation* v. *AIM Enterprises, Inc.;* Complaint for Patent Infringement and Demand for Jury Trial; 08 CV 01659 (MHB); Sep. 9, 2008.
*I-Flow Corporation* v. *Biomet Texas, Inc.;* Plaintiff's Complaint for Patent Infringement; 08 CV 01602 (O); Sep. 11, 2008.
*I-Flow Corporation* v. *Apex Medical Technologies, Inc.;* Complaint for Patent Infringement, Demand For Jury Trial, 07 CV 1200 DMS (NLS); Jun. 29, 2007.
*I-Flow Corporation* v. *Apex Medical Technologies, Inc.;* Defendant's Answer to Plaintiff's Complaint For Patent Infringement And Counterclaim; 07 CV 1200 DMS (NLS); Sep. 19, 2007.
*I-Flow Corporation* v. *Apex Medical Technologies, Inc.;* Defendant's First Amended Answer To Plaintiff's Complaint For Patent Infringement And Counterclaim;07 CV 1200 DMS (NLS); Oct. 26, 2007.
*I-Flow Corporation* v. *Apex Medical Technologies, Inc.;* Plaintiff's Reply to Defendant's First Amended Answer And Counterclaims; 07 CV 1200 DMS (NLS); Nov. 13, 2007.
*I-Flow Corporation* v. *Apex Medical Technologies, Inc.;* First Amended Complaint For Patent Infringement; Trade Secret Misappropriation; Breach of Confidence; And Common Law And Statutory Unfair Competition; 07 CV 1200 DMS (NLS); Nov. 27, 2007.
*I-Flow Corporation* v. *Apex Medical Technologies, Inc.;* Second Amended Complaint For Patent Infringement; Trade Secret Misappropriation; Breach of Confidence; And Common Law And Statutory Unfair Competition; 07 CV 1200 DMS (NLS); Jan. 14, 2008.
*I-Flow Corporation* v. *Apex Medical Technologies, Inc.;* Plaintiff I-Flow Corporation's Preliminary Claim Construction And Identification Of Extrinsic Evidence Pursuant To Patent L.R. 4.1; 07 CV 1200 DMS (NLS); Feb. 25, 2008.
*I-Flow Corporation* v. *Apex Medical Technologies, Inc.;* Apex Preliminary Proposed Claim Constructions; 07 CV 1200 DMS (NLS); Feb. 25, 2008.
*I-Flow Corporation* v. *Zone Medical, LLC.;* Complaint for Patent Infringement, Demand for Jury Trial; 08cv 0057 JAH WMc; Jan. 10, 2008.
*I-Flow Corporation* v. *Apex Medical Technologies, Inc.;* Plaintiff I-Flow Corporation's Responsive Claim Construction Pursuant to Patent Local Rule 4.1(c) and (d), 07 CV 1200 DMS (NLS); Mar. 10, 2008.
*I-Flow Corporation* v. *Apex Medical Technologies, Inc.;* Apex Responsive Claim Constructions, 07 CV 1200 DMS (NLS); Mar. 10, 2008.
*I-Flow Corporation* v. *Apex Medical Technologies, Inc.;* Joint Claim Construction Chart, Worksheet, and Hearing Statement Pursuant to Local Rule 4.2, 07 CV 1200 DMS (NLS); Mar. 24, 2008.
*I-Flow Corp.* v. *West Cost Aesthetics,* Case No. 8:08–cv–00784–AG–RNB, Complaint.
*I-Flow Corp.* v. *Apex Medical Technologies, Inc.,* Case No. 07–cv–1200 DMS (NLS), Order Construing Patent Claims.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 23–28 are cancelled.

Claims 1, 6, 11 and 14–15 are determined to be patentable as amended.

Claims 2–5, 7–10, 12–13 and 16–22, dependent on an amended claim, are determined to be patentable.

New claims 29 and 30 are added and determined to be patentable.

1. A compact portable apparatus for dispensing a liquid under pressure at a substantially constant flow rate over a period of time comprising:
    an elongated generally cylindrical support member;
    elongated elastic sleeve means mounted and sealingly secured at fixed spaced longitudinal positions on said support member for defining a substantially zero non-pressurized volume pressure reservoir for holding a liquid in a pressurized state for dispensing therefrom;
    housing means comprising collapsible non-stretchable housing means for containing said support member and said pressure reservoir for enabling said pressure reservoir to expand naturally and for confining said reservoir to fill concentrically about said support member, *said collapsible non-stretchable housing means loosely positioned around said sleeve means and defining a chamber between said sleeve means and said collapsible non-stretchable housing means*;
    inlet means for introducing a liquid into said elastic pressure reservoir; and
    outlet means for dispensing liquid from said pressure reservoir to a selected site.

6. An apparatus for dispensing a liquid under pressure according to claim 5 wherein said [said] O-rings are each covered by a cup shaped removeably attached to the ends of said support member.

11. An apparatus for dispensing a liquid under pressure according to claim 10 wherein said [said] O-rings are each covered by a cup shaped cap removeably attached to the ends of said support member.

14. An apparatus for dispensing liquid under pressure according to claim 1 wherein said housing means comprises a substantially [shperical] *spherical* rigid housing formed of like half-shells hinged together.

15. A compact collapsible infusion apparatus for dispensing a liquid under pressure at a predetermined substantially constant flow rate over a period of time comprising:
    an elongated generally cylindrical support member having inlet means including an inlet port in one end of said member, and outlet means including an outlet port in the other end of said member;
    elongated elastic sleeve means mounted in non-stretched surface contact and sealingly secured at fixed spaced longitudinal positions on said support member for defining a substantially zero non-pressurized volume pressure reservoir for holding a liquid in a pressurized state for dispensing therefrom;
    first housing means including a collapsible shell enclosing said support member and said pressure reservoir, said housing *means* having a size and shape for enabling said pressure reservoir to expand naturally and for confining said reservoir to fill concentrically about said support member, *said collapsible shell loosely positioned around said sleeve means and defining a chamber between said sleeve means and said collapsible shell*;
    inlet means in one end of said support member for introducing a liquid into said elastic pressure reservoir; and
    outlet means in the other end of said support member for dispensing liquid from said pressure reservoir to a selected site.

*29. An apparatus for dispensing a liquid under pressure according to claim 1, wherein said chamber is substantially spherical around said sleeve means.*

*30. An apparatus for dispensing a liquid under pressure according to claim 15, wherein said chamber is substantially spherical around said sleeve means.*

\* \* \* \* \*